United States Patent [19]

Nielsen et al.

[11] Patent Number: 4,844,415
[45] Date of Patent: Jul. 4, 1989

[54] VALVE

[75] Inventors: Ole S. M. Nielsen, Holte; Franz Primdahl, Helsingor, both of Denmark

[73] Assignee: Asicomo A/S, Denmark

[21] Appl. No.: 147,563

[22] Filed: Jan. 19, 1988

Related U.S. Application Data

[63] Continuation of Ser. No. 890,190, filed as PCT DK85/0011 on Nov. 26, 1985, published as W086/03271 on Jun. 5, 1986, abandoned.

[30] Foreign Application Priority Data

Nov. 26, 1984 [DK] Denmark ............................. 5605/84

[51] Int. Cl.$^4$ ............................................... F16K 3/26
[52] U.S. Cl. ...................................... 251/325; 251/96; 251/100; 251/296
[58] Field of Search ................... 251/96, 100, 296, 325

[56] References Cited

U.S. PATENT DOCUMENTS

| | | | |
|---|---|---|---|
| 508,275 | 11/1893 | Brodt | 251/96 |
| 668,406 | 2/1901 | Holt | 251/96 |
| 927,161 | 7/1909 | Paul | 251/325 X |
| 1,759,433 | 5/1930 | Carmosin | 251/96 |

FOREIGN PATENT DOCUMENTS

| | | |
|---|---|---|
| 1450469 | 12/1968 | Fed. Rep. of Germany . |
| 1957135 | 5/1971 | Fed. Rep. of Germany . |
| 2549188 | 5/1976 | Fed. Rep. of Germany . |
| 1503783 | 3/1978 | United Kingdom . |

*Primary Examiner*—Robert G. Nilson
*Attorney, Agent, or Firm*—Pollock, VandeSande & Priddy

[57] ABSTRACT

A valve, which is especially suited for use in connection with a urine bag, has a cylindrical valve body, which is displaceably and rotatably mounted in a tubular valve housing having a transverse flow passage defined therein. A projection formed at one end of the valve body may be brought into engagement with a cut-out or notch in the adjacent end of the valve housing. In this position in which the projection engages with the notch, the valve is open, because the transverse bore of the valve body is aligned with the flow passage. The valve may be closed by displacing the valve body in relation to the valve housing so as to bring the projection out of engagement with the notch, and the valve body may be rotated in relation to the valve housing, if desired. The engagement between the projection and the notch ensures that the transverse bore of the valve body extends coaxially with the flow passage in the open position of the valve.

3 Claims, 1 Drawing Sheet

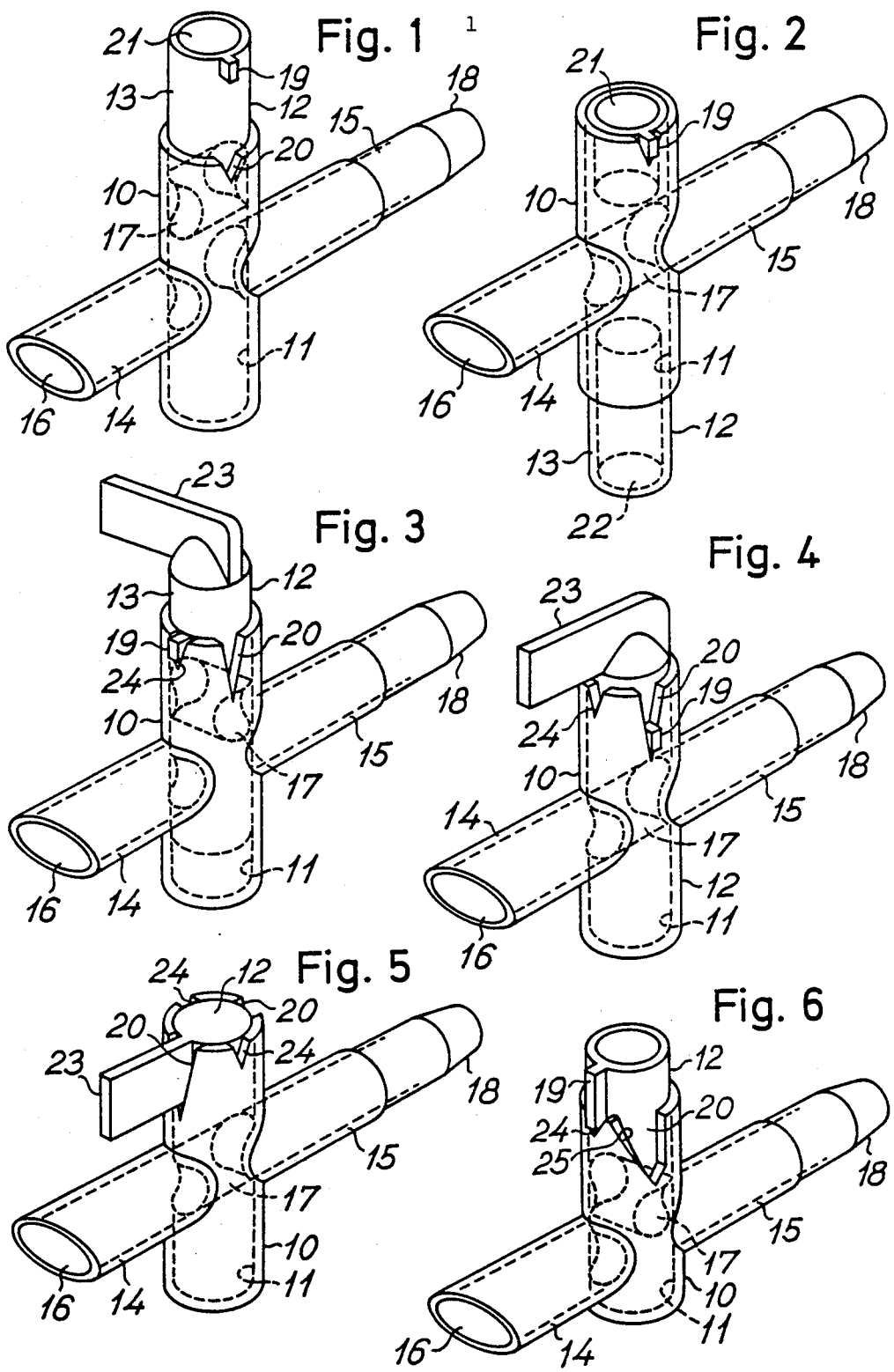

VALVE

This application is a continuation of Ser. No. 890,190, filed as PCT DK85/00111 on Nov. 26, 1985, published as WO86/03271 on Jun. 5, 1986, now abandoned.

FIELD OF THE INVENTION

The present invention relates to a valve comprising a housing having defined therein a longitudinally extending bore and a flow passage extending transversely to and intersecting said longitudinal bore the valve further has a valve body defining a transverse through-bore therein and being sealingly received in said longitudinal bore of the valve housing so as to be displaceable between an open position of the valve, in which the transverse bore of the valve body is aligned with the flow passage of the housing and a closed position of the valve in which the transverse bore of the valve body and the flow passage of the housing are mutually displaced.

BACKGROUND OF THE INVENTION

When valves are to be used in connection with urine bags and other disposable articles, it is important that the valve functions reliably and is easy to operate, even though the valve must be cheap to manufacture. A valve of the above type having a tubular valve housing and a circularly cylindrical valve body displaceably arranged therein is known from, e.g. British patent specification No. 1,310,581. The end portions of the valve body of this known valve have an outer diameter corresponding to the diameter of the longitudinal bore of the housing which receives the valve body so that these end portions are in sealing engagement with the inner wall of the housing, while the central portion of the valve body between these end portions has a reduced diameter. In this known valve the valve body may be displaced between an open position of the valve, in which the central portion of the valve body with the reduced diameter is arranged opposite to a transverse flow passage intersecting the longitudinal bore of the housing, and a closed position of the valve, in which one of the thicker end portions of the valve body is located opposite to and closes the flow passage. This known valve structure has the advantage that its function is independent of the rotational position of the valve body in relation to the valve housing. However, the molding of a valve body with a central portion of a reduced diameter requires the use of a relatively complicated injection mold. Furthermore, in order to obtain a reasonably small flow resistance, it is desirable to make the diameter of the central portion of the valve body relatively small, which may, however, unduly reduce the strength of the central portion of the valve body.

It is also known to avoid the use of a valve body with a reduced central portion by providing the valve body with a transverse bore. In order to ensure that this transverse bore of the valve body is always aligned with the flow passage of the valve housing in the open position of the valve, the valve body must be prevented from rotating in relation to the valve housing. In the last mentioned known structure this is obtained by forming the longitudinal bore of the valve housing as well as the valve body with a cross-section shaped like a circle with a segment cut therefrom. This cross-sectional shape has, however, proved less satisfactory because it requires that the measures of the outer peripheral wall of the valve body and the inner peripheral wall of the valve housing are kept within very narrow limits in order to ensure sealing engagement between these surfaces.

SUMMARY OF THE INVENTION

The present invention provides a valve of the above type, wherein the interengaging peripheral surfaces of the valve housing and the valve body may have a circular cylindrical shape within the total sealing area, whereby a sufficient seal may be obtained between these surfaces.

The valve according to the invention is characterized in that the inner wall of the housing defining the longitudinal bore and the outer peripheral surface of the valve body have a circular cylindrical shape, and cooperating axially extending guide means arranged at one end of the housing and at the adjacent end of the valve body, respectively, and having such axial extension and peripheral position that the guide means are in mutual engagement in the open position of the valve and out of engagement in the closed position of the valve. In the valve according to the invention, the guide means are formed at one end of the valve housing and the adjacent end of the valve body so that they are axially spaced from the transverse bore of the valve body as well as from the flow passage of the valve housing. Therefore, these guide means do not have any negative influence on the seal obtainable between the outer peripheral surface of the valve body and the inner peripheral surface of the valve housing. However, the valve body cannot be moved to the position in which the valve is open without the guide means being brought into mutual engagement, thereby it is ensured that in the open position of the valve the valve body is maintained in such a rotational position in relation to the valve housing that the transverse bore of the valve body is aligned with the flow passage of the valve, housing. In the closed position of the valve the guide means are out of engagement with each other. In this position of the valve according to the invention the valve body may therefore be rotated to a rotational position in which the axis of the transverse bore of the valve body forms an acute or right angle with the axis of the flow passage defined in the housing, whereby the risk of leakage is further reduced in the closed position of the valve.

The guide means may have any suitable form and may, for example, be interengaging formations of the interengaging peripheral surfaces of the valve body and the valve housing, respectively. Alternatively, the guide means may be arranged outside the valve housing. In the presently preferred embodiment, the guide means comprises a first cut-out or notch formed at said one end of the peripheral wall of the valve housing and a radially extending projection formed on the valve body. In the closed position of the valve, the valve body may be rotated freely, because the said projection is out of engagement with the adjacent end portion of the valve housing. However, when the valve body is displaced to the open position of the valve, it has to be rotated so that the projection may be brought into engagement with the cut-out or notch formed at the adjacent end of the peripheral wall of the valve housing receiving the valve body.

The projection formed on the valve body may have great or small radial extension and may possibly have such a shape and size that it may serve as a hand grip or handle by means of which the valve body may be rotated and displaced axially. The valve body may be moved between its open and closed positions by a mere axial displacement. However, as mentioned above, this axial displacement may preferably be combined with a rotational movement. In the last mentioned case it may be desirable to fix the rotational position which is considered the optimum closing position. Therefore, the valve according to the invention may have positioning means for defining a closed position of the valve in which the angular position of the valve body in relation to the valve housing is different from that of the open position of the valve. These positioning means may, for example, be adapted to define an angle of about 90° between the relative angular positions of the valve body in the said open and closed positions of the valve, respectively.

When the guide means comprises a radially extending projection formed on the valve body, the positioning means may advantageously comprise a second cut-out or notch formed at said one end of the peripheral wall of the valve housing and angularly offset in relation to said first cut-out or notch. If the axial extension of the said second cut-out or notch forming part of the positioning means is relatively long, it may be possible to push the valve body axially inward into the valve housing in the closed position of the valve, so that the transverse bore of the valve body is positioned rather close to the flow passage defined in the housing even though the axis of the flow passage and the axis of the transverse bore define an angle therebetween. Therefore, the longitudinal extension of said second cut-out or notch is preferably substantially smaller than that of the guide means.

When the projection formed on the valve body is in the form of a handle or hand grip, the valve body may be axially displaced and rotated by means of this hand grip as described above. However, the axial length of the valve body preferably exceeds the axial length of the longitudinal bore of the housing by an amount equal to or greater than the axial extension of the guide means. The valve body may then be moved between its open and closed positions by pushing the end of the valve body extending from the valve housing axially into the housing.

In the valve according to the invention, the axial extension of the guide means may in principle be smaller than the diameter of the transverse bore defined in the valve body, because the axial displacement of the valve body may be combined with a rotational movement of the body as explained above. However, in the preferred embodiment of the valve according to the invention, the axial extension of the guide means is equal to or greater than the diameter of the transverse bore of the valve body. The valve may then be closed by a pure axial displacement of the valve body; and if it is desired to improve the sealing efficiency; the valve body may further be rotated in relation to the valve housing.

Even though the valve according to the invention is especially suited for use in connection with plastic urine bags and similar disposable articles, it may also be used for any other purpose for which a simple and manually operable valve may be used. The valve housing as well as the valve body are preferably made from plastic material, whereby the valve may be produced at specially low costs. However, in principle, the valve according to the invention may of course also be made from any other suitable material, such as metal.

BRIEF DESCRIPTION OF THE DRAWINGS

The invention will now be further described with reference to the drawings, wherein FIGS. 1 and 2 show a first embodiment of the valve according to the invention in its closed and open position, respectively, FIGS. 3 and 4 show a second embodiment of the valve according to the invention in its closed and open position, respectively, FIG. 5 shows a third embodiment of the valve according to the invention in its open position, and FIG. 6 shows a fourth embodiment of the valve according to the invention.

DESCRIPTION OF THE PREFERRED EMBODIMENT

The valves shown in the drawings comprise a tubular valve housing 10 with a circular cylindrical inner surface 11 defining a through-bore which receives a valve body 12 with a slide fit. The valve body has a circular cylindrical outer peripheral surface 13, which is in sealing engagement with the inner surface 11 of the valve housing. A pair of transversely extending, diametrically oppositely directed pipe stubs 14 and 15 define a flow passage 16 extending transversely to and intersecting the bore of the tubular housing 10. A transverse bore 17 with a cross-section corresponding substantially to the cross-section of the flow passage 16 is formed in the central portion of the valve body 12. The valves shown in the drawings are preferably made from plastic by die casting and are especially well suited for use in connection with urine bags and similar disposable articles. Therefore, the free end 18 of the pipe stub 15 is adapted to be received in a connecting hose, not shown, and may be tapered in order to facilitate the insertion in the hose.

In the embodiment shown in FIGS. 1 and 2, the valve body 12 has an axial length exceeding the axial length of the tubular valve housing 10 by an amount exceeding the diameter of the transverse bore 17. At one end the valve body 12 is provided with a radially extending projection 19 which is adapted to engage with a V-shaped cut-out or notch 20 formed in the adjacent end portion of the housing 10. In order to reduce the consumption of material, the end portions of the valve body 12 may be hollow so as to define cavities 21 and 22 open at the end surfaces of the valve body, while the central portion of the valve body in which the transverse bore 17 is formed may be solid.

The mutual arrangement of the projection 19, the transverse bore 17, the notch 20 and the flow passage 16 is such that the transverse bore 17 extends parallel with the flow passage 16 when the projection 19 is arranged opposite to the notch 20. The distance between the transverse bore 17 and the projection 19 is such that the transverse bore 17 will be substantialy aligned with the flow passage 16, when the projection 19 has been brought into engagement with the notch or cut-out 20. In this position, which is illustrated in FIG. 2, the valve is open, and liquid or gas may freely flow through the part of the flow passage 16 defined by the pipe stub 15, through the transverse bore 17 of the valve body 12, and through the part of the flow passage 16 defined by the pipe stub 14. The valve may be closed by pushing the end portion of the valve body 12 extending downwards from the valve housing 10 in FIG. 2 inwards into the valve housing until the adjacent end surface of the valve body 12 becomes substantially coplanar with the adjacent end surface of the valve housing 10 as shown in FIG. 1. In this closed position the transverse bore 17 extends parallel with and is displaced in relation to the flow passage 16. Furthermore, the valve body 12 may be rotated through an angle of for example about 90° in relation to the valve housing, if desired, whereby the sealing efficiency of the valve is increased, which may be advantageous, especially if the axial displacement of the valve body 12 does not substantially exceed the diameter of the transverse bore 17. When the valve is to be opened again, the valve body is rotated to a position in which the projection 19 is opposite to the V-shaped notch or cut-out 20, whereafter the valve body 12 is moved axially until the projection 19 has been brought into engagement with the cut-out or notch 20.

In the embodiment shown in FIGS. 3 and 4, the axial length of the valve body 12 corresponds substantially to the axial length of the tubular valve housing 10, and at one end the valve body 12 is provided with a finger grip or handle 23. In FIGS. 3 and 4 the axial extension of the V-shaped notch or cut-out 20 exceeds that in FIGS. 1 and 2, and the projection 19 is correspondingly spaced from the end of the valve body which is provided with the handle 23. The end of the valve housing having the notch 20 formed therein is provided with a further notch or cut-out 24 with an axial extension which is substantially smaller than that of the notch 20, and the notch 24 is displaced at an angle of about 90° in relation to the notch 20.

When the projection 19 has been inserted into the notch 20 as shown in FIG. 4, the transverse bore 17 of the valve body 12 is aligned with the flow passage 16, and the valve is open. When the valve is to be closed the handle 23 is gripped, and the valve body 12 is pulled outwards so as to bring the projection 19 out of engagement with the notch 20. Thereafter the valve body is rotated about 90° so that the projection 19 may be brought into engagement with the cut-out or notch 24 as shown in FIG. 3. The transverse bore 17 will now partly be displaced in parallel in relation to the flow passage and partly rotated in relation thereto, and the valve is now in its closed position.

In the embodiment shown in FIG. 5, the handle 23 is formed so as to replace the projection 19, and a notch or cut-out 20 is formed at two diametrically opposite locations at one end of the valve housing 10. Correspondingly, a smaller notch 24 is formed at two diametrically oppositely arranged positions each of which is angularly displaced in relation to the notches 20 by about 90°. In FIG. 5 the handle 23 is received in one of the notches 20 and the valve is in its open position. Such an open position of the valve could also be obtained by moving the handle 23 into engagement with the other of the V-shaped notches or cut-outs 20. When the valve is to be closed, the valve body 12 is axially displaced so that the handle 23 is brought out of engagement with the respective notch 20, whereafter the valve body is rotated about 90° so that it may be pushed into engagement with one of the V-shaped notches 24, whereby the valve is closed.

In the embodiment shown in FIG. 6, the notch or cut-out 20 determining the open position of the valve has a substantially helical edge portion 25 which extends into the notch 24 determining the closed position of the valve. The edge portion 25 may then serve as a cam along which the projection 19 may slide when the valve body 12 is moved between its open and closed positions and vice versa. Thus, the movement of the valve body will be a combined displacing and rotating movement. In the embodiment shown in FIG. 6, the axial extensions of the notches 20 and 24 are such that when moved between its open and closed positions the valve body is axially displaced through a distance which is somewhat smaller than the diameter of the flow passage 16 and of the transverse bore 17. The valve may then have a relatively small dimension in the axial direction of the tubular housing 10.

It should be understood that various modifications of the embodiments described above may be made within the scope of the present invention. As an example, each of the embodiments shown in FIGS. 1–4 may be provided with two diametrically oppositely arranged notches or cut-outs 20 so that two closing positions of the valves are obtained. It should be understood that while the valve according to the present invention has been described specifically as being suitable for use in connection with urine bags, the valve may also be used for any other purpose where a cheap and efficiently operating valve of the type described is needed. As an example, the valve according to the invention may be used in connection with infusion equipment and similar hospital articles.

I claim:

1. A valve of the disposable type comprising a housing defining therein a longitudinally extending, circular cylindrical through-bore and a flow passage extending transversely to and intersecting said longitudinal through-bore, a valve body having defined therein a transverse through-bore and being sealingly received in said longitudinal through-bore of the valve housing so as to be rotable and freely axially displaceable therein between an open position of the valve in which the transverse bore of the valve body is aligned with the flow passage of the housing and a closed position of the valve in which the transverse bore of the valve body and the flow passage of the housing are mutually displaced, and cooperating axially extending guide means arranged at one end of the housing and at an adjacent end of the valve body, respectively, and having such axial extension and peripheral position that the guide means are in mutual engagement in the open position of the valve and out of engagement in the other of said positions of the valve, the axial length of the valve body exceeding the axial length of the longitudinal through-bore of the housing by an amount at least equal to the axial extension of the cross-sectional area of the transverse through-bore, whereby one of the ends of the valve body freely accessibly extends from the housing in the closed position of the valve, while the other end of the valve body freely accessibly extends from the housing in the open position of the valve.

2. A valve according to claim 1, wherein the guide means comprise a first cut-out formed at said one end of the peripheral wall of the valve housing and a radially extending projection formed on the valve body.

3. A valve according to claim 1, wherein the axial length of the valve body exceeds the axial length of the longitudinal through-bore of the housing by an amount at least equal to the axial extension of the guide means.

* * * * *